(12) United States Patent
Stumpf

(10) Patent No.: US 8,685,996 B2
(45) Date of Patent: Apr. 1, 2014

(54) METHODS FOR MAKING 3-O-PROTECTED MORPHINONES AND 3-O-PROTECTED MORPHINONE DIENOL CARBOXYLATES

(75) Inventor: Andreas Stumpf, Dublin, CA (US)

(73) Assignee: Purdue Pharma L.P., Stamford, CT (US)

(*) Notice: Subject to any disclaimer, the term of this patent is extended or adjusted under 35 U.S.C. 154(b) by 0 days.

(21) Appl. No.: 13/472,227

(22) Filed: May 15, 2012

(65) Prior Publication Data
US 2012/0225902 A1  Sep. 6, 2012

Related U.S. Application Data

(62) Division of application No. 13/189,228, filed on Jul. 22, 2011, now Pat. No. 8,198,444, which is a division of application No. 10/588,637, filed as application No. PCT/US2005/003390 on Feb. 4, 2005, now Pat. No. 8,003,793.

(60) Provisional application No. 60/542,711, filed on Feb. 6, 2004.

(51) Int. Cl.
*A61K 31/485* (2006.01)
*C07D 489/02* (2006.01)

(52) U.S. Cl.
USPC .... 514/282; 546/44; 252/183.13; 252/186.35

(58) Field of Classification Search
USPC ........... 252/183.13, 182.31, 186.35; 514/282; 546/44
See application file for complete search history.

(56) References Cited

U.S. PATENT DOCUMENTS

| | | | |
|---|---|---|---|
| 2,654,756 | A | 10/1953 | Homeyer et al. |
| 4,025,520 | A | 5/1977 | Grew et al. |
| 4,472,253 | A | 9/1984 | Schwartz |
| 5,112,975 | A | 5/1992 | Wallace |
| 5,821,374 | A | 10/1998 | Jenny et al. |
| 5,869,669 | A | 2/1999 | Huang et al. |
| 5,908,846 | A | 6/1999 | Bungaard et al. |
| 6,008,355 | A | 12/1999 | Huang et al. |
| 6,013,796 | A | 1/2000 | Huang et al. |
| 6,046,313 | A | 4/2000 | Scheinmann et al. |
| 6,177,567 | B1 | 1/2001 | Chiu et al. |
| 6,262,266 | B1 | 7/2001 | Chiu et al. |
| 2003/0073848 | A1 | 4/2003 | Shieh et al. |

FOREIGN PATENT DOCUMENTS

DE           902257       1/1954
WO    WO 2005/077957 A3  5/2006

OTHER PUBLICATIONS

Corey et al., "A New and Highly Effective Method for the Oxidation of Primary and Secondary Alcohols to Carbonyl Compounds," *J. Amer. Chem. Soc.*, 94(21):7586-7587 (1972).

"Cyanuric and Isocyanuric Acids," *Kirk Othmer Encyclopedia of Chemical Technology*, vol. 7, pp. 397-409 (1979).
De Luca et al., "A Mild and Efficient Alternative to the Classical Swern Oxidation," *J. Org. Chem.* 66:7907-7909 (2001).
European Search Report for Application No. EP 05712726.8, dated Feb. 8, 2007.
European Search Report for Application No. EP 07014411, dated Jan. 9, 2008.
Greene et al., "Protective Groups in Organic Synthesis," 3rd Ed., pp. 246-248 & 273-276, John Wiley & Sons, Inc., New York (1999).
Harris et al., "Modification of the Swern Oxidation: Use of a Soluble Polymer-bound, Recyclable, and Odorless Sulfoxide," *J. Org. Chem.* 63:2407-2409 (1998).
Ninan et al., "An Improved Synthesis of Noroxymorphone," *Tetrahedron* 48(32):6709-6716 (1992).
Nishide et al., "New Odorless Protocols for the Swern and Corey-Kim Oxidations," *Tetrahedron Let.* 43:5177-5179 (2002).
Ohsugi et al., "New Odorless Method for the Corey-Kim and Swern Oxidations Utilizing Dodecyl Methyl Sulfide (Dod-S-Me)," *Tetrahedron* 59:8393-8398 (2003).
Partial European Search Report for Application No. EP 09015220, dated Apr. 21, 2010.
Paterson et al., "Qualitative Screening for Drugs of Abuse in Hair Using GC-MS," *J. Anal. Toxicology* 25(3):203-208 (2001).
PCT International Search Report for International Application No. PCT/US2005/003390, dated Oct. 18, 2005.
PCT Written Opinion for International Application No. PCT/US2005/003390, dated Oct. 18, 2005.
Tilstam et al., "Trichloroisocyanuric Acid: A Safe and Efficient Oxidant," *Org. Process Res. & Devel.* 6(4):384-393 (2002).
Xiong et al., "A Selective and Convenient Oxidation of Sulfides to Sulfoxides with Trichloroisocyanuric Acid," *Synthetic Comm.* 31(2):245-248 (2001).
Tojo et al., Chapter 2 (portions) entitled "Activated Dimethyl Sulfoxide," pp. 97-100 and 141-179 in "Oxidation of Alcohols to Aldehyde and Ketones—A Guide to Current Common Practice," Springer, New York (2006).

*Primary Examiner* — Charanjit Aulakh
(74) *Attorney, Agent, or Firm* — Dechert LLP

(57) ABSTRACT

Disclosed are methods for making aldehydes and ketones comprising allowing the corresponding primary or secondary alcohol to react in the presence of trichoroisocyanuric acid, a compound of formula $R_1SR_2$ and a base. In one embodiment, the alcohol is a compound of formula (I):

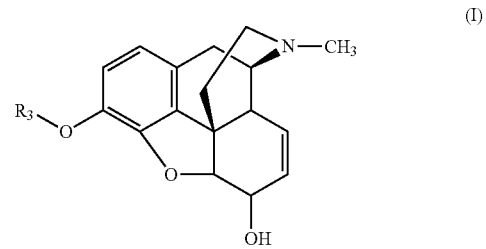

wherein $R_3$ is a protecting group.

Also disclosed are methods for making 3-O-protected morphine dienol carboxylates comprising allowing a compound of formula (I) to oxidize in the presence of a chlorine-containing compound and a compound of formula $R_1SR_2$; and allowing the product of the oxidation step to react with an acylating agent.

23 Claims, No Drawings

US 8,685,996 B2

METHODS FOR MAKING 3-O-PROTECTED MORPHINONES AND 3-O-PROTECTED MORPHINONE DIENOL CARBOXYLATES

This application is a divisional of application Ser. No. 13/189,228, filed Jul. 22, 2011, now U.S. Pat. No. 8,198,444 B2, which is a divisional of application Ser. No. 10/588,637, filed Aug. 4, 2006, now U.S. Pat. No. 8,003,793 B2, which is the U.S. national stage of international application serial no. PCT/US2005/003390, filed Feb. 4, 2005, which claims the benefit under 35 U.S.C. §119(e) of provisional application No. 60/542,711, filed Feb. 6, 2004, the contents of all of which are incorporated herein by reference.

1. FIELD OF THE INVENTION

The present invention relates to methods for making 3-O-protected morphinones and 3-O-protected morphinone dienol carboxylates. The present invention also relates to methods for making aldehydes and ketones from the corresponding primary and secondary alcohols, respectively.

2. BACKGROUND OF THE INVENTION

Morphine and structural analogs of morphine (the "morphine alkaloids") such as codeine, hydrocodone, hydromorphone, naloxone, naltrexone, oxycodone and oxymorphone are used in analgesic prescription drugs. Other morphine analogs, e.g., thebaine, are useful starting materials for preparing analgesic morphine alkaloids. However, thebaine is only a minor component of the morphine alkaloids found in the seeds of poppy plants, and synthetic methods for preparing thebaine are relatively costly (see U.S. Pat. No. 6,262,266 B1 to Chiu et al.).

Codeinone dienol acetate, which is the 3-O-methyl derivative of morphinone dienol acetate, is a morphine alkaloid useful for preparing analgesic and antagonistic morphine alkaloids such as naloxone, naltrexone and oxycodone (see, e.g., U.S. Pat. No. 6,013,796 to Huang et al.). Codeinone dienol acetate can be prepared by oxidation of codeine to codeinone followed by acylation (see, e.g., U.S. Pat. No. 6,013,796 to Huang et al.).

Other 3-O-protected-morphinone dienol carboxylates are known and are generally prepared by oxidation of the corresponding 3-O-protected-morphine followed by acylation. A number of these 3-O-protected-morphinone dienol carboxylates have been used to prepare other useful morphine alkaloids.

The following paragraphs relate to known methods for making 3-O-protected morphinones by oxidation of the corresponding 3-O-protected morphines.

Codeine is 3-O-methylmorphine and codeinone is 3-O-methylmorphinone.

U.S. Pat. No. 2,654,756 to Homeyer et al. describes the reaction of codeine with aluminum tri(tert-butoxide) and methoxycyclohexanone in toluene to form codeinone, with yield of codeinone reported to be less than 50%.

Ninan et al., Tetrahedron 48:6709-6716 (1992) describes the reaction of 3-O-dimethyl-t-butylsilylmorphine with manganese dioxide in chloroform at 25° C. to form 3-O-dimethyl-t-butylsilylmorphinone.

The Ninan et al. reference also describes the reaction of 3-O-dimethyl-t-butylsilylmorphine with tetrapropyl ammonium perruthenate and N-methylmorpholine-N-oxide in dichloromethane at an unspecified temperature to form 3-O-dimethyl-t-butylsilylmorphinone in about 86% yield.

U.S. Pat. No. 6,013,796 to Huang et al. describes the reaction of 3-O-acetylmorphine with a complex formed of dimethylsulfoxide ("DMSO") and oxalyl chloride in the presence of base (the "Swern oxidation process") at −78° C. to provide the corresponding 3-acetylmorphinone in 73% yield. U.S. Pat. No. 6,013,796 also describes reacting 3-O-benzylmorphine under similar conditions to provide 3-O-benzylmorphinone in 65% yield. However, the described process requires at least 2.5 molar equivalents of DMSO per mole of morphine and generates malodorous dimethylsulfide as a by-product.

Despite these described methods, there remains a need for improved methods for making 3-O-protected morphinones.

The Swern oxidation process described above has been the focus of considerable research, because it avoids the use of aggressive inorganic oxidants such as $MnO_2$ and is generally useful for oxidizing primary and secondary alcohols to aldehydes and ketones, respectively. For example, De Luca et al., J. Org. Chem. 66:7907-7909 (2001) describes the reaction of primary or secondary alcohols with a complex formed of DMSO and trichorocyanuric acid ("TCCA") in tetrahydrofuran ("THF") at −30° C. in the presence of triethylamine to provide the corresponding aldehydes and ketones, respectively. However, malodorous dimethylsulfide is formed as a by-product of the reaction. Accordingly, much effort has been spent modifying the Swern oxidation process or developing more attractive alternatives.

The following paragraphs relate to known modifications and alternatives to the Swern oxidation processes.

Nishide et al., Tetrahedron. Lett. 43:5177-5179 (2002) describes a low-odor Swern oxidation process using dodecylmethylsulfoxide as the sulfoxide reactant.

Harris et al., J. Org. Chem. 63:2407-2409 (1998) describes a low-odor Swern oxidation process using polymer bound 6-(methylsulfinyl)hexanoic acid as the sulfoxide reactant, and the sulfoxide reactant can be regenerated by reaction of the sulfide by-product with $NaIO_4$.

An alternative to the Swern reaction is described in Corey et al., J. Am. Chem. Soc. 94:7586-7587 (1972), where a primary or secondary alcohol is reacted with a complex formed of dimethylsulfide and N-chlorosuccinamide ("NCS") or $Cl_2$ at −25° C. in the presence of a base (the "Corey-Kim oxidation") to form the corresponding aldehyde and ketone, respectively. However, the Corey reference discloses that reaction of 2-cyclohexenol forms chlorocyclohexene rather than 2-cyclohexenone. Additionally, the described process uses malodorous dimethylsulfide as a reagent.

Ohsugi et al., Tetrahedron 59:8393-8398 (1992) describes a low-odor Corey-Kim oxidation process where a primary or secondary alcohol is reacted with $CH_3S(C_{12}H_{25})$ and NCS in the presence of triethylamine at −40° C., but the described process uses at least a 3-fold molar excess of the sulfide and NCS per mole of alcohol.

Despite these described methods, there remains a need for improved methods for oxidizing primary or secondary alcohols to the corresponding aldehydes or ketones, respectively.

Citation of any reference in Section 2 of this application is not an admission that the reference is prior art to the application.

3. SUMMARY OF THE INVENTION

The present invention relates to methods for forming an aldehyde or ketone from the corresponding primary or secondary alcohol, respectively.

In one embodiment, the invention relates to methods for making a ketone, comprising allowing a secondary alcohol to react in the presence of a compound of formula $R_1SR_2$, trichloroisocyanuric acid and a base under conditions sufficient to make the ketone, wherein $R_1$ and $R_2$ are each independently —$(C_1$-$C_{20})$alkyl, —$(C_3$-$C_8)$cycloalkyl or -phenyl.

In another embodiment, the present invention relates to methods for making an aldehyde, comprising allowing a primary alcohol to react in the presence of a compound of formula $R_1SR_2$, trichloroisocyanuric acid and a base under conditions sufficient to make the aldehyde, wherein $R_1$ and $R_2$ are each independently —$(C_1$-$C_{20})$alkyl, —$(C_3$-$C_8)$cycloalkyl or -phenyl.

The present invention also relates to methods for making 3-O-protected morphinones.

In one embodiment, the invention relates to methods for making a compound of formula (II):

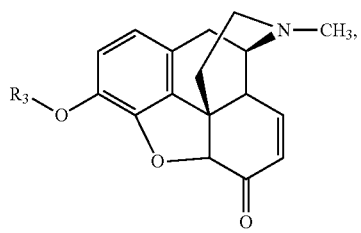

(II)

comprising, allowing a compound of formula (I):

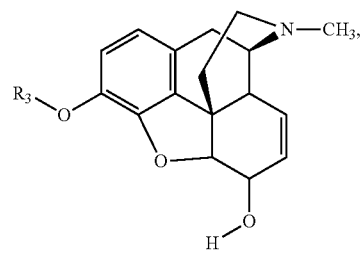

(I)

to react in the presence of a compound of formula $R_1SR_2$ and a chlorine-containing reagent under conditions sufficient to make the compound of formula (II), wherein:

$R_1$ and $R_2$ are each independently —$(C_1$-$C_{20})$alkyl, —$(C_3$-$C_8)$cycloalkyl or -phenyl; and $R_3$ is a protecting group.

The present invention also relates to methods for making 3-O-protected dienol carboxylate derivatives of morphinone.

In one embodiment, the present invention relates to methods for making a compound of formula (III):

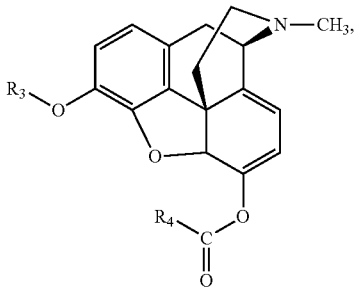

(III)

comprising:

(a) allowing a compound of formula (I):

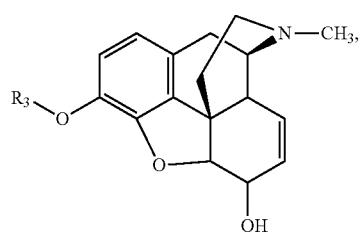

(I)

to react in the presence of a compound of formula $R_1SR_2$ and a chlorine-containing reagent under conditions sufficient to make a mixture comprising a compound of

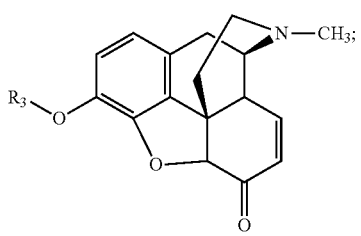

(II)

and (b) allowing the compound of formula (II) to react with a first base and an acylating agent of formula $R_4C(O)OC(O)R_4$ or $R_4C(O)X$ under conditions sufficient to make the compound of formula (III), wherein:

$R_1$ and $R_2$ are each independently —$(C_1$-$C_{20})$alkyl, —$(C_3$-$C_8)$cycloalkyl or -phenyl;

$R_3$ is a protecting group; and $R_4$ is —$(C_1$-$C_{10})$alkyl; and

X is —Cl, —Br or —I.

The present invention also relates to novel compositions useful for oxidizing a primary or secondary alcohol to an aldehyde or ketone, respectively.

In one embodiment, the present invention relates to compositions comprising a compound of formula $R_1SR_2$, trichloroisocyanuric acid and a base, wherein $R_1$ and $R_2$ are each independently —$(C_1$-$C_{20})$alkyl or —$(C_3$-$C_8)$cycloalkyl or -phenyl.

The present invention also relates to novel 3-O-protected dienol carboxylate derivatives of morphinone.

In one embodiment, the present invention relates to compounds of formula (III), wherein:

$R_3$ is —Si$((C_1$-$C_{10})$alkyl$)_3$, —Si(aryl)$(C_1$-$C_{10})$alkyl$)_2$, or —Si(aryl)$_2(C_1$-$C_{10})$alkyl); and $R_4$ is —$(C_1$-$C_{10})$alkyl.

The present invention can be understood more fully by reference to the following detailed description and illustrative examples, which exemplify non-limiting embodiments of the invention.

4. DETAILED DESCRIPTION OF THE INVENTION

4.1. Definitions

As used herein, the generic phrase "3-O-protected morphine" refers to the compound having the structure of formula (I):

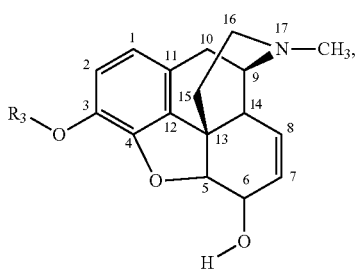

(I)

wherein $R_3$ is a protecting group.

A compound of formula (Ia) has the structure:

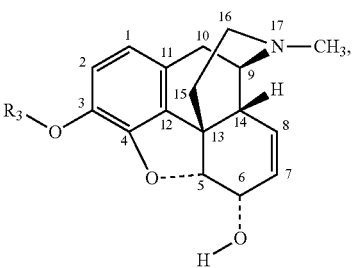

(Ia)

wherein $R_3$ is a protecting group.

As used herein, the generic phrase "3-O-protected morphinone" refers to the compound having the structure of formula (II):

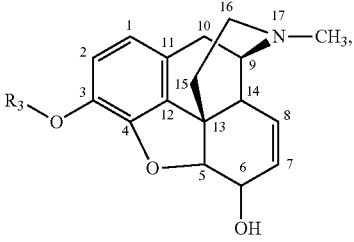

(II)

wherein $R_3$ is a protecting group.

The compound of formula (IIa) has the structure:

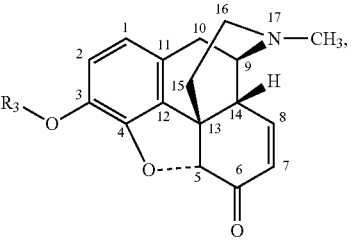

(IIa)

wherein $R_3$ is a protecting group.

As used herein, the generic phrase "3-O-protected morphinone dienol carboxylate" refers to the compound having the structure of formula (III):

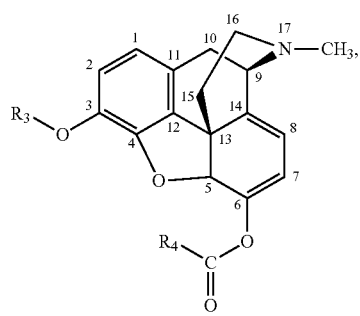

(III)

wherein $R_3$ is a protecting group, and $R_4$ is a —$(C_1$-$C_{10})$alkyl.

The compound of formula (IIIa) has the structure:

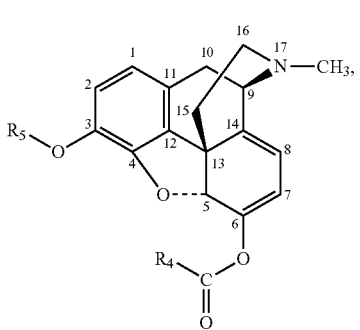

(IIIa)

wherein $R_3$ is a protecting group, and $R_4$ is a —$(C_1$-$C_{10})$alkyl.

As used herein, the term "halo" refers to —F, —Cl, —Br or —I.

As used herein, the term "—$(C_1$-$C_{10})$alkyl" means a saturated straight-chain or branch-chain hydrocarbon having from 1 to 10 carbon atoms. Representative saturated straight chain $(C_1$-$C_{10})$alkyls are -methyl, -ethyl, -n-propyl, -n-butyl, -n-pentyl, -n-hexyl, -n-heptyl, -n-octyl, -n-nonyl and -n-decyl. Representative saturated branched —$(C_1$-$C_{10})$alkyls are -isopropyl, -sec-butyl, -isobutyl, -tert-butyl, and the like.

As used herein, the term "—$(C_1$-$C_{20})$alkyl" means a saturated straight-chain or branched hydrocarbon having from 1 to 20 carbon atoms. Representative saturated straight chain $(C_1$-$C_{20})$alkyls are -methyl, -ethyl, -n-propyl, -n-butyl, -n-pentyl, -n-hexyl, -n-heptyl, -n-octyl, -n-nonyl, -n-decyl, -n-undecyl, -n-dodecyl, -n-tridecyl, -n-tetredecyl, -n-pentadecyl, -n-hexadecyl, -n-heptadecyl, -n-octadecyl, -n-nonadecyl, and -n-eicosyl. Non-limiting examples of saturated branched —$(C_1$-$C_{20})$alkyls are -isopropyl, -sec-butyl, -iso-butyl, -tert-butyl, and the like.

As used herein, the phrase "protecting group" means a group other than —H which is useful for protecting the 3-O-position of the morphine, morphinone and morphinone dienol carboxylate from unwanted reactions. The protecting group can, if desired, be replaced with —H or another group after forming the compound of formula (III).

As used herein, the phrase "anhydrous" when used in reference to an organic solvent, unless otherwise defined herein, means an organic solvent having an amount of water that is less than about 0.01% by weight of the total amount of water and organic solvent.

As used herein, the phrase "chlorine-containing reagent" when used in reference to the morphinone-forming method or morphinone-forming step refers to a compound or complex having a reactive chlorine that is useful for promoting the formation of the compound of formula (II) from the compound of formula (I)

As used herein, the term "isolating" when used in reference to a mixture comprising a compound of formula (II) or (III) means separating the compound of formula (II) or (III) from the organic solvent, when present, and water, when present.

4.2. Methods for Oxidizing Primary or Secondary Alcohols

As noted above, the present invention relates to methods for oxidizing a primary or secondary alcohol to form an aldehyde or ketone, respectively (the "carbonyl-forming method"). Compared to known methods, the present methods for oxidizing primary or secondary alcohols can be carried out under milder conditions and/or with more efficient utilization of reagents than conventional processes.

In one embodiment, the carbonyl-forming method comprises the use of a low-odor oxidation process.

In one embodiment, the present invention relates to a method for making a ketone, comprising allowing a secondary alcohol to react in the presence of a compound of formula $R_1SR_2$, trichloroisocyanuric acid and a base under conditions sufficient to make the ketone, wherein $R_1$ and $R_2$ are each independently —$(C_1-C_{20})$alkyl, —$(C_3-C_8)$cycloalkyl or -phenyl.

Non-limiting examples of useful secondary alcohols include straight-chain and branch-chain alkyl, alkenyl, and alkynyl primary alcohols including 2-propanol, 2-butanol, 2-pentanol, 3-methylbutan-2-ol, 2-hexanol, 3-methyl-2-pentanol, 4-methyl-2-pentanol, 3-hexanol, 2-methyl-3-pentanol, 2-heptanol, 3-methyl-2-hexanol, 4-methyl-2-hexanol, 5-methyl-2-hexanol, 3-ethyl-2-pentanol, 3,3-dimethyl-2-pentanol, 3,4-dimethyl-2-pentanol, 4,4-dimethyl-2-pentanol, 3-heptanol, 2-methyl-3-heptanol, 4-methyl-3-heptanol, 5-methyl-3-heptanol, 2,2-dimethyl-3-pentanol, 2,4-dimethyl-3-pentanol, 2-ethyl-3-pentanol, 4-ethyl-3-pentanol, 4-heptanol, and the like; cyclic secondary alcohols such as cyclohexanol; the compounds of formula (I) or (Ia) wherein $R_3$ is a protecting group; alkylaryl secondary alcohols such as 1-phenyl-1-ethanol, 1-phenyl-1-propanol, 1-phenyl-1-propanol, and the like; dialkyl secondary alcohols such as diphenylmethanol; oligomeric and polymeric alcohols such as oligomers and polymers of polyvinylalcohol; and the like.

In one embodiment, the carbonyl-forming method comprises the use of a compound of formula (I), wherein $R_3$ is a protecting group.

In one embodiment, the carbonyl-forming method comprises the use of a secondary alcohol of formula (Ia).

Non-limiting examples of protecting groups useful when the carbonyl-forming method comprises the compounds of formula (I) include —$(C_1-C_{10})$alkyl; -benzyl; acyls such as —$C(O)(C_1-C_{10})$alkyl and —$C(O)C_6H_5$; carbonates such as —$C(O)O(C_1-C_{10})$alkyl); silyls such as —$Si(C_1-C_{10})$alkyl)$_3$, —$Si(aryl)((C_1-C_{10})alkyl)_2$, and —$Si(aryl)_2((C_1-C_{10})alkyl)$; phosphineoxides such as —$P(O)(CH_3)_2$; phosphinesulfides such as —$P(S)(CH_3)_2$; and arylsulfonates such as —$S(O)OC_6H_4$-p-$CH_3$.

In one embodiment, the carbonyl-forming method comprises the use of a compound of formula (I), wherein $R_3$ is —$(C_1-C_{10})$alkyl, -benzyl, —$C(O)(C_1-C_{10})$alkyl, —$C(O)O(C_1-C_{10})$alkyl), —$Si((C_1-C_{10})alkyl)_3$, —$Si(aryl)((C_1-C_{10})alkyl)_2$, —$Si(aryl)_2((C_1-C_{10})alkyl)$, —$P(O)((—P(S)((C_1-C_{10})alkyl)_2$, or —$S(O)OC_6H_4$-p-$CH_3$.

In one embodiment, the carbonyl-forming method comprises the use of a compound of formula (I), wherein $R_3$ is —$CH_3$.

In another embodiment, the carbonyl-forming method comprises the use of a compound of formula (I), wherein $R_3$ is —$Si((C_1-C_{10})alkyl)_3$, —$Si(aryl)(C_1-C_{10})alkyl)_2$, or —$Si(aryl)_2(C_1-C_{10})alkyl)$.

In another embodiment, the carbonyl-forming method comprises the use of a compound of formula (I), wherein $R_3$ is —$Si((C_1-C_{10})alkyl)_3$.

In another embodiment, the carbonyl-forming method comprises the use of a compound of formula (I), wherein $R_3$ is —$Si(CH_3)_2(C(CH_3)_3)$.

In another embodiment, the present invention relates to a method for making an aldehyde, comprising allowing a primary alcohol to react in the presence of a compound of formula $R_1SR_2$, trichloroisocyanuric acid and a base under conditions sufficient to make the aldehyde, wherein $R_1$ and $R_2$ are each independently —$(C_1-C_{20})$alkyl, —$(C_3-C_8)$cycloalkyl or -phenyl.

Non-limiting examples of primary alcohols useful in the carbonyl-forming method include, but are not limited to, straight-chain and branch-chain alkyl, alkenyl, and alkynyl primary alcohols such as methanol, ethanol, n-propanol, n-butanol, 2-methylpropanol, n-pentanol, 2-methylbutanol, 3-methylbutanol, n-hexanol, 2-methylpentanol, 3-methylpentanol, 4-methylpentanol, 2,2-dimethylbutanol, 2,3-dimethylbutanol, 3,3-dimethylbutanol, 2-ethylbutanol, n-heptanol, n-octanol, n-nonanol, n-decanol, and the like.

In one embodiment, the carbonyl-forming method comprises the use of a compound of formula $R_1SR_2$, wherein $R_1$ is -methyl and $R_2$ is —$(C_1-C_{20})$alkyl, —$(C_3-C_8)$cycloalkyl or -phenyl.

In another embodiment, the carbonyl-forming method comprises the use of a compound of formula $R_1SR_2$, wherein $R_1$ is —$CH_3$ and $R_2$ is —$(C_1-C_{20})$alkyl.

In another embodiment, the carbonyl-forming method comprises the use of a compound of formula $R_1SR_2$, wherein $R_1$ is —$CH_3$ and $R_2$ is —$(C_{12})$alkyl.

The base is an organic base or an inorganic base. Non-limiting examples of organic bases useful in the carbonyl-forming method include, but are not limited to, organic amines such as, e.g., trialkylamines such as trimethylamine, triethylamine, tri-n-propylamine, tri-n-butylamine, diethylmethylamine, dimethylethylamine, diisopropylethylamine, and the like; aryldialkylamines such as dimethylphenylamine and diethylphenylamine; pyridine and pyridine substituted with one or more —$(C_1-C_4)$alkyl such as 2-methylpyridine, 3-methylpyridine, 4-methylpyridine, 2,3-dimethylpyridine, 2,4-dimethylpyridine, 2,5-dimethylpyridine, 3,4-dimethylpyridine, 3,5-dimethylpyridine, 2,3,4-trimethylpyridine, 2,3,5-trimethylpyridine, 2,4,5-dimethylpyridine, 3,4,5-trimethylpyridine, and the like; pyridine substituted with dialkylamino groups such as para-N,N-dimethylaminopyridine; alkali metal salts of weak acids such as, e.g., lithium, sodium, potassium, rubidium and cesium carboxylates; and any combination thereof.

Non-limiting examples of inorganic bases useful in the carbonyl-forming method include the hydroxides of the alkali metals such as lithium, sodium, potassium, rubidium and cesium.

In one embodiment, the base is an organic base. In another embodiment, the organic base is an organic amine. In another embodiment, the organic amine is triethylamine, diisopropylethylamine, pyridine, dimethylpyridine or dimethylaminopyridine. In another embodiment, the organic amine is triethylamine.

In another embodiment, the base is an inorganic base.

Compounds of formula (I) and (Ia) are commercially available or can be prepared by methods described in Section 4.3.

Trichloroisocyanuric acid is available from Aldrich Chemical Co., Milwaukee, Wis.

Compounds of formula $R_1SR_2$ are commercially available from Lancaster Synthesis, Windham, N.H., or can be prepared by reacting a compound of formula $R_1SH$ with $K_2CO_3$ and $R_2I$ in dimethylformamide as described in Ohsugi et al., *Tetrahedron* 59:8393-8398 (2003).

In one embodiment, the amount of alcohol used in the carbonyl-forming method ranges from about 1.0 to about 9.0 molar equivalents per molar equivalent of trichloroisocyanuric acid; in another embodiment, the amount of alcohol used in the carbonyl-forming method ranges from about 2.0 to about 5.0 molar equivalents per molar equivalent of trichloroisocyanuric acid; and in another embodiment, the amount of alcohol used in the carbonyl-forming method ranges from about 2.0 to about 4.0 molar equivalents per molar equivalent of trichloroisocyanuric acid.

In one embodiment, the amount of compound of formula $R_1SR_2$ used in the carbonyl-forming method ranges from about 1.0 to about 9.0 molar equivalents per molar equivalent of trichloroisocyanuric acid; in another embodiment, the amount of compound of formula $R_1SR_2$ used in the carbonyl-forming method ranges from about 2.0 to about 5.0 molar equivalents per molar equivalent of trichloroisocyanuric acid; and in another embodiment, the amount of compound of formula $R_1SR_2$ used in the carbonyl-forming method ranges from about 2.5 to about 3.5 molar equivalents per molar equivalent of trichloroisocyanuric acid.

In one embodiment, the amount of base used in the carbonyl-forming method ranges from about 1.0 to about 15.0 molar equivalents per molar equivalent of trichloroisocyanuric acid; in another embodiment, the amount of base used in the carbonyl-forming method ranges from about 2.0 to about 10.0 molar equivalents per molar equivalent of trichloroisocyanuric acid; and in another embodiment, the amount of base used in the carbonyl-forming method ranges from about 2.5 to about 7.0 molar equivalents per molar equivalent of trichloroisocyanuric acid.

In one embodiment, the carbonyl-forming method is carried out in the presence of an organic solvent. Non-limiting examples of organic solvents that are useful in the carbonyl-forming method include, but are not limited to aromatic hydrocarbons such as benzene, toluene, xylene, mesitylene, chlorobenzene; $(C_1-C_4)$halogenated hydrocarbons such as dichloromethane, chloroform, carbon tetrachloride and dichloroethane; ethers such as diethyl ether, dipropyl ether, dibutyl ether, methyl-tert-butyl ether, tetrahydrofuran, methyltetrahydrofuran; and ethyl acetate.

In one embodiment, the organic solvent when used in the carbonyl-forming method is benzene, toluene, xylene, mesitylene, chlorobenzene, dichloromethane, chloroform, carbon tetrachloride, dichloroethane, diethyl ether, dipropyl ether, di-butyl ether, methyl-tert-butyl ether, tetrahydrofuran, ethyl acetate, or any combination thereof.

In another embodiment, the organic solvent when used in the carbonyl-forming method is or includes dichloromethane.

In another embodiment, the organic solvent is or includes toluene.

In one embodiment, the organic solvent when used in the carbonyl-forming method is present in an amount ranging from about 0.1 parts by weight up to about 50 parts by weight based on the weight of the compound of formula $R_1SR_2$. In another embodiment, the organic solvent when used in the carbonyl-forming method is present in an amount ranging from about 0.1 parts by weight up to about 25 parts by weight based on the weight of the compound of formula $R_1SR_2$. In another embodiment, the organic solvent when used in the carbonyl-forming method is present in an amount ranging from about 0.1 parts by weight up to about 10 parts by weight based on the weight of the compound of formula $R_1SR_2$.

In one embodiment, the organic solvent when used in the carbonyl-forming method is anhydrous. Anhydrous organic solvents are commercially available or can be obtained by contacting the organic solvent with a suitable dehydrating agent such as, e.g., molecular sieves; reactive metals such as Li, Na or K, and mixtures thereof; metal hydrides such as CaH or $LiAlK_s$; and metal and metalloid oxides such as BaO, CaO and $P_2O_5$ (see Amarego et al., *Purification of Laboratory Chemicals* (4th ed. 1996); and Gordan et al., *The Chemist's Companion* 445-447 (1972)). The amount of water in the organic solvent can be determined by, e.g., Karl-Fisher titration (see ASTM E1064-00 and ASTM E203-01).

The carbonyl-forming method is carried under conditions that are sufficient to make an aldehyde or ketone. In one embodiment, the carbonyl-forming method is carried out until at least about 80 mole percent of the alcohol has been converted to an aldehyde or a ketone; in another embodiment, the carbonyl-forming method is carried out until at least about 95 mole percent of the alcohol has been converted to an aldehyde or a ketone; and in another embodiment, the carbonyl-forming method is carried out until at least about 99 mole percent of the alcohol has been converted to an aldehyde or a ketone.

The progress of the carbonyl-forming method can be monitored using conventional analytical techniques, including, but not limited to, thin-layer chromatography ("TLC"), high-performance liquid chromatography ("HPLC"), gas chromatography ("GC"), gas-liquid chromatography ("GLC"), infrared spectroscopy ("IR") and nuclear magnetic resonance spectroscopy ("NMR") such as $^1H$ or $^{13}C$ NMR.

Typically, a time that is sufficient to carry out the carbonyl-forming method ranges from about 0.25 hours to about 20 hours; in another embodiment, a time that is sufficient to carry out the carbonyl-forming method ranges from about 0.5 hours to about 10 hours; and in another embodiment, a time that is sufficient to carry out the carbonyl-forming method ranges from about 1 hours to about 5 hours.

Typically, a temperature that is sufficient to carry out the carbonyl-forming method ranges from about -78° C. to about 130° C.; in another embodiment, a temperature that is sufficient to carry out the carbonyl-forming method ranges from about -50° C. to about 50° C.; and in another embodiment, a temperature that is sufficient to carry out the carbonyl-forming method ranges from about -40° C. to about 50° C.

The carbonyl-forming method can be carried out at reduced pressure, atmospheric pressure or elevated pressure. In one embodiment, the carbonyl-forming method is carried out at atmospheric pressure.

In another embodiment, the carbonyl forming step is carried out under an inert atmosphere such as, e.g., $N_2$, He, Ne, Ar, Kr, Xe, or any combination thereof. In one embodiment, the carbonyl forming step is carried out under a $N_2$ atmosphere.

The order of addition of the compound of formula $R_1SR_2$, trichloroisocyanuric acid, primary or secondary alcohol, base and organic solvent, if any, can vary. Examples are as follows.

In one non-limiting embodiment, the carbonyl-forming method is carried out by adding a primary or secondary alcohol, optionally in the presence of an organic solvent, to an admixture comprising a compound of formula $R_1SR_2$, trichlorisocyanuric acid and a base, optionally in the presence of an organic solvent.

In another non-limiting embodiment, the carbonyl-forming method is carried out by adding an admixture comprising a compound of formula $R_1SR_2$, trichlorisocyanuric acid and a base, optionally in the presence of an organic solvent, to a primary or secondary alcohol, optionally in the presence of an organic solvent.

In another non-limiting embodiment, the carbonyl-forming method is carried out by adding a base, optionally in the presence of an organic solvent, to an admixture comprising a compound of formula $R_1SR_2$ and trichlorisocyanuric acid, optionally in the presence of an organic solvent, followed by addition of a primary or secondary alcohol, optionally in the presence of an organic solvent.

In another non-limiting embodiment, the carbonyl-forming method is carried out by adding an admixture comprising a compound of formula $R_1SR_2$ and trichlorisocyanuric acid, optionally in the presence of an organic solvent, to a base, optionally in the presence of an organic solvent, followed by addition of a primary or secondary alcohol, optionally in the presence of an organic solvent.

In another non-limiting embodiment, the carbonyl-forming method is carried out by adding a primary or secondary alcohol, optionally in the presence of an organic solvent, to an admixture comprising a compound of formula $R_1SR_2$ and trichlorisocyanuric acid, optionally in the presence of an organic solvent, followed by addition of a base, optionally in the presence of an organic solvent.

In another non-limiting embodiment, the carbonyl-forming method is carried out by adding a compound of formula (I), optionally in the presence of an organic solvent, to an admixture comprising a compound of formula $R_1SR_2$ and trichlorisocyanuric acid, optionally in the presence of an organic solvent, followed by addition of a base, optionally in the presence of an organic solvent.

In another non-limiting embodiment, the carbonyl-forming method is carried out by adding a base, optionally in the presence of an organic solvent, to an admixture comprising a compound of formula $R_1SR_2$ and trichlorisocyanuric acid, optionally in the presence of an organic solvent, followed by addition of a compound of formula (I), optionally in the presence of an organic solvent.

The aldehyde or ketone formed in the carbonyl-forming method can be isolated and purified by methods known in the art. For example, a reaction mixture comprising an aldehyde or ketone can be purified by fractional distillation; chromatography on silica, alumina or FLORISIL™; and/or recystallization. Where the reaction mixture comprising an aldehyde or ketone further comprises an organic solvent, all or part of the organic solvent can optionally be removed, typically via evaporation, prior to purification.

Non-limiting examples of organic solvents useful as chromatography eluents include straight-chain and branch chain aliphatic $(C_4-C_{10})$hydrocarbons such as butanes, pentanes, hexanes, heptanes, octanes, nonanes, and decanes; aliphatic cyclic $(C_4-C_7)$hydrocarbons such as cyclobutane, cylcopentane, cyclohexane and cycloheptane; aromatic hydrocarbons such as benzene, toluene and xylene; each of which can be substituted with one or more -halo groups.

Other non-limiting examples of organic solvents useful as chromatography eluents include $(C_1-C_4)$halogenated hydrocarbons such as chloromethane, methylene chloride, chloroform and carbon tetrachloride; $(C_1-C_{10})$aliphatic alcohols such as methanol, ethanol, n-propanol, isopropanol, n-butanol, sec-butanol, isobutanol, tert-butanol, n-pentantol, n-hexanol, n-heptanol, n-octanol, n-nonanol, n-decanol, and the like; dialkyl ethers such as diethyl ether, diisopropyl ether, dibutyl ethers and methyl butyl ethers; diaryl ethers such as diphenyl ether; cyclic ethers such as tetrahydrofuran and dioxane; glymes such as ethylene glycol dimethyl ether, ethyl acetate; dimethylsulfoxide; N-methylpyrrolidinone; hexamethylphosphoramide; dimethylformamide; and any mixture thereof.

In one embodiment, the organic solvent used as chromatography eluent comprises an aliphatic hydrocarbon and an ether.

The present invention further relates to compositions comprising a primary or secondary alcohol, a compound of formula $R_1SR_2$ as defined herein, trichloroisocyanuric acid and a base. These compositions are useful for making a ketone or an aldehyde, as described above.

Non-limiting examples of primary or secondary alcohols, compounds of formula $R_1SR_2$, trichloroisocyanuric acid and bases include those described above for the carbonyl-forming method.

In another embodiment, the invention relates to a composition comprising a compound of formula $R_1SR_2$, trichloroisocyanuric acid, a base and a compound of formula (I), wherein $R_3$ is a protecting group.

In another embodiment, the invention relates to a composition comprising a compound of formula $R_1SR_2$, trichloroisocyanuric acid, a base and a compound of formula (I), wherein $R_3$ is —$(C_1-C_{10})$alkyl, -benzyl, —$C(O)(C_1-C_{10})$alkyl, —$C(O)O(C_1-C_{10})$alkyl), —$Si((C_1-C_{10})$alkyl$)_3$, —$Si(aryl)((C_1-C_{10})$alkyl$)_2$, —$Si(aryl)_2((C_1-C_{10})$alkyl), —$P(O)((C_1-C_{10})$alkyl$)_2$, —$P(S)((C_1-C_{10})$alkyl$)_2$, or —$S(O)OC_6H_4$-p-$CH_3$.

In another embodiment, the invention relates to a composition comprising a compound of formula $R_1SR_2$, trichloroisocyanuric acid, a base and a compound of formula (I), wherein $R_3$ is —$Si(C_1-C_{10})$alkyl$)_3$, —$Si(aryl)(C_1-C_{10})$alkyl$)_2$, or —$Si(aryl)_2(C_1-C_{10})$alkyl.

In another embodiment, the invention relates to a composition comprising a compound of formula $R_1SR_2$, trichloroisocyanuric acid, a base and a compound of formula (I), wherein $R_3$ is —$Si((C_1-C_{10})$alkyl$)_3$.

In another embodiment, the invention relates to a composition comprising a compound of formula $R_1SR_2$, trichloroisocyanuric acid, a base and a compound of formula (I), wherein $R_3$ is —$Si(CH_3)_2(C(CH_3)_3)$.

In another embodiment, the invention relates to a composition comprising a compound of formula $R_1SR_2$, trichloroisocyanuric acid, a base and a compound of formula (I), wherein $R_3$ is —$CH_3$.

In another embodiment, the compositions comprising a primary or secondary alcohol, a compound of formula $R_1SR_2$, and trichloroisocyanuric acid can further comprise an organic solvent. Non-limiting examples of organic solvents include those described above for the carbonyl-forming method.

The relative molar amounts of primary or secondary alcohol, a compound of formula $R_1SR_2$, trichloroisocyanuric acid and a base, and the relative amount of organic solvent, when present, are those described above for the carbonyl-forming method.

4.3. Methods for Making Morphinones

In another embodiment, the present invention relates to methods for making a compound of formula (II) (the "morphinone-forming method") comprising allowing a compound of formula (I) to react in the presence of a compound of formula $R_1SR_2$ and a chlorine-containing reagent under conditions sufficient to make the compound of formula (II), wherein:

$R_1$ and $R_2$ are each independently —$(C_1$-$C_{20})$alkyl, —$(C_3$-$C_8)$cycloalkyl or -phenyl; and $R_3$ is a protecting group.

In one embodiment, the compound of formula (I) is the compound of formula (Ia), and the compound of formula (II) is the compound of formula (IIIa).

In one embodiment, the morphinone-forming method comprises the use of a compound of formula (I), wherein $R_3$ is —$(C_1$-$C_{10})$alkyl, -benzyl, —$C(O)(C_1$-$C_{10})$alkyl, —$C(O)O(C_1$-$C_{10})$alkyl), —$Si((C_1$-$C_{10})$alkyl)$_3$, —$Si(aryl)((C_1$-$C_{10})$alkyl)$_2$, —$Si(aryl)_2((C_1$-$C_{10})$alkyl)$, —$P(O)((C_1$-$C_{10})$alkyl)$_2$, —$P(S)((C_1$-$C_{10})$alkyl)$_2$, or —$S(O)OC_6H_4$-p-$CH_3$.

In another embodiment, the morphinone-forming method comprises the use of a compound of formula (I), wherein $R_3$ is —$Si((C_1$-$C_{10})$alkyl)$_3$, —$Si(aryl)(C_1$-$C_{10})$alkyl)$_2$, or —$Si(aryl)_2(C_1$-$C_{10})$alkyl).

In another embodiment, the morphinone-forming method comprises the use of a compound of formula (I), wherein $R_3$ is —$Si((C_1$-$C_{10})$alkyl)$_3$.

In another embodiment, the morphinone-forming method comprises the use of a compound of formula (I), wherein $R_3$ is —$Si(CH_3)_2(C(CH_3)_3)$.

In another embodiment, the morphinone-forming method comprises the use of a compound of formula (I), wherein $R_3$ is —$CH_3$.

Non-limiting examples of compounds of formula $R_1SR_2$ useful in the morphinone-forming method include those described in Section 4.2 for the carbonyl-forming method. In one embodiment, $R_1$ is —$CH_3$ and $R_2$ is —$(C_{12})$alkyl.

Non-limiting examples of chlorine-containing reagents useful in the morphinone-forming method include N-chloroamines such as trichloroisocyanuric acid, N-chlorosuccinimide, salts of dichloroisocyanuric acid such as sodium dichloroisocyanurate, 1,3-dichloro-5,5-dimethylhydantoin; $Cl_2$; and hypochlorites such as calcium hypochlorite.

In one embodiment, the chloro-containing reagent used in the morphinone-forming method is trichloroisocyanuric acid, N-chlorosuccinimide, sodium dichloroisocyanurate, 1,3-dichloro-5,5-dimethylhydantoin, $Cl_2$, calcium hypochlorite, or any mixture thereof.

In another embodiment, the chloro-containing reagent used in the morphinone-forming method is trichloroisocyanuric acid.

In another embodiment, the chloro-containing reagent used in the morphinone-forming method is N-chlorosuccinimide.

In another embodiment, the chloro-containing reagent used in the morphinone-forming method is $Cl_2$.

Compounds of formula (I) can be prepared by known methods useful for protecting a phenolic hydroxy group (see, e.g., Greene et al., *Protective Groups in Organic Synthesis* 143-170 (1991), which is incorporated herein by reference).

Compounds of formula (I) where $R_3$ is —$(C_1$-$C_{10})$alkyl are commercially available or can be made by allowing morphine to react with a halo$(C_1$-$C_{10})$alkyl in dimethoxyethane and in the presence of tetraethylammonium fluoride at 20° C. as described in T. W. Greene et al., *Protective Groups in Organic Synthesis* 146 (1991) and in U.S. Patent Application Publication No. 200310073848 A1.

Compounds of formula (I) where $R_3$ is —$Si((C_1$-$C_{10})$alkyl)$_3$, —$Si(aryl)(C_1$-$C_{10})$alkyl)$_2$, or —$Si(aryl)_2(C_1$-$C_{10})$alkyl) can be prepared by allowing morphine to react with Na metal or butyllithium, and allowing the resultant complex to react with $ClSi(C_1$-$C_{10})$alkyl)$_3$, $ClSi(aryl)(C_1$-$C_{10})$alkyl)$_2$ or $ClSi(aryl)_2(C_1$-$C_{10})$alkyl) as described in Ninan et al., *Tetrahedron* 48:6709-6716 (1992) and in U.S. Pat. No. 6,046,313 to Scheinmann et al. for the synthesis of 3-O-dimethyl-t-butylsilylmorphine. Alternatively, the 3-O-silyl derivatives of morphine can be prepared by allowing morphine to react with $ClSi(C_1$-$C_{10})$alkyl)$_3$, $ClSi(aryl)(C_1$-$C_{10})$alkyl)$_2$ or $ClSi(aryl)_2(C_1$-$C_{10})$alkyl) in a polar organic solvent and in the presence of base as described in Section 5.1 for the compound of formula (I) where $R_3$ is —$Si(CH_3)_2(C(CH_3)_3)$.

Compounds of formula (I) where $R_3$ is —$C(O)(C_1$-$C_{10})$alkyl can be prepared by allowing morphine hydrochloride to react with a compound of formula $(C_1$-$C_{10})C(O)OC(O)(C_1$-$C_{10})$ in aqueous sodium bicarbonate as described in U.S. Pat. No. 5,908,846 to Bundgaard et al.

Compounds of formula (I) where $R_3$ is -benzyl can be prepared by allowing morphine to react with benzylbromide and NaOH in aqueous methanol at 25° C. as described in U.S. Pat. No. 6,013,796 to Huang et al.

Compounds of formula (I) where $R_3$ is —$C(O)O(C_1$-$C_{10})$alkyl can be prepared by allowing morphine to react with a compound of formula $ClC(O)O(C_1$-$C_{10})$alkyl in chloroform and in the presence of sodium bicarbonate under refluxing conditions as described in U.S. Pat. No. 5,112,975 to Wallace.

Trichloroisocyanuric acid, N-chlorosuccinimide, sodium dichloroisocyanurate, 1,3-dichloro-5,5-dimethylhydantoin and calcium hypochlorite are available from Aldrich Chemical Co., Milwaukee, Wis.

When $Cl_2$ is the chlorine-containing reagent, the $O_2$ can be in the form of a gas or solution. The gas form of $Cl_2$ is available from Matheson, Montgomeryville, Pa., and can be added to the reaction admixture by, for example, bubbling the $Cl_2$ into the admixture. The rate and amount of $Cl_2$ addition can be controlled by methods known in the art using, for example, gas flow regulators and/or meters.

The solution form of $Cl_2$ can be prepared by allowing gaseous $Cl_2$ to dissolve in a suitable organic solvent. The concentration of $Cl_2$ in the solution can be determined by analytical methods known in the art.

Without being limited by theory, Applicant believes that the chlorine-containing reagent reacts with the compound of formula $R_1SR_2$ to form a sulfonium cation:

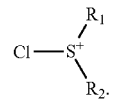

The sulfonium compound then reacts with the hydroxyl group of the primary or secondary alcohol to form the carbonyl group.

In one embodiment, the amount of compound of formula (I) used in the morphinone-forming method ranges from about 1.0 to about 9.0 molar equivalents per molar equivalent of the chlorine-containing reagent; in another embodiment, the amount of compound of formula (I) used in the morphinone-forming method ranges from about 2.0 to about 5.0 molar equivalents per molar equivalent of the chlorine-containing reagent; and in another embodiment, the amount of compound of formula (I) used in the morphinone-forming method ranges from about 2.0 to about 4.0 molar equivalents per molar equivalent of the chlorine-containing reagent.

In one embodiment, the amount of compound of formula $R_1SR_2$ used in the morphinone-forming method ranges about 1.0 to about 9.0 molar equivalents per molar equivalent of the chlorine-containing reagent; in another embodiment, the amount of the compound of formula $R_1SR_2$ used in the morphinone-forming method ranges from about 2.0 to about 5.0 molar equivalents per molar equivalent of the chlorine-containing reagent; and in another embodiment, the amount of the compound of formula $R_1SR_2$ used in the morphinone-forming method ranges from about 2.5 to about 3.5 molar equivalents per molar equivalent of the chlorine-containing reagent.

In one embodiment, the amount of the chlorine-containing reagent used in the morphinone-forming method ranges from about 1.0 to about 9.0 molar equivalents per molar equivalent of the compound of formula (I); in another embodiment, the amount of the chlorine-containing reagent used in the morphinone-forming method ranges from about 2.0 to about 5.0 per molar equivalent of the compound of formula (I); and in another embodiment, the amount of the chlorine-containing reagent used in the morphinone-forming method ranges from about 2.0 to about 4.0 per molar equivalent of the compound of formula (I).

In certain embodiments, the morphinone-forming method may further comprise the use of a base. Non-limiting examples of useful bases include those organic bases and inorganic bases described in Section 4.2 for the carbonyl-forming method.

In one embodiment the base is an organic base. In one embodiment, the organic base is triethylamine or para-N,N-dimethylaminopyridine.

In another embodiment, the base is an inorganic base.

In one embodiment, the amount of base when used in the morphinone-forming method ranges from about 1.0 to about 15.0 molar equivalents per molar equivalent of the chlorine-containing reagent; in another embodiment, the amount of base when used in the morphinone-forming method ranges from about 2.0 to about 10.0 molar equivalents per molar equivalent of the chlorine-containing reagent; and in another embodiment, the amount of base when used in the morphinone-forming method ranges from about 2.5 to about 7.0 molar equivalents per molar equivalent of the chlorine-containing reagent.

In certain embodiments, the morphinone-forming method may further comprise the use of an organic solvent. Non-limiting examples of useful organic solvents include those noted above for the carbonyl-forming method. In one embodiment, the organic solvent is dichloromethane.

In one embodiment, the organic solvent when used in the morphinone-forming method is present in an amount ranging from about 0.1 parts by weight up to about 50 parts by weight based on the weight of the compound of formula (I); in another embodiment, the organic solvent when used in the morphinone-forming method is present in an amount ranging from about 0.1 parts by weight up to about 25 parts by weight based on the weight of the compound of formula (I); and in another embodiment, the organic solvent when used in the morphinone-forming method is present in an amount ranging from about 0.1 parts by weight up to about 10 parts by weight based on the weight of the compound of formula (I).

In one embodiment, the organic solvent is anhydrous. Methods for preparing anhydrous solvents are described in Section 4.2 for the carbonyl-forming method.

The morphinone-forming method is carried under conditions that are sufficient to make the compound of formula (II). In one non-limiting embodiment, the morphinone-forming method is carried out until at least about 80 mole percent of the compound of formula (I) has been converted to the compound of formula (II); in another non-limiting embodiment, the morphinone-forming method is carried out until at least about 95 mole percent of the compound of formula (I) has been converted to the compound of formula (II); and in another non-limiting embodiment, the morphinone-forming method is carried out until at least about 99 mole percent of the compound of formula (I) has been converted to the compound of formula (II).

The progress of the morphinone-forming method can be monitored using conventional analytical techniques comparable to those described in Section 4.2 for monitoring the carbonyl-forming method.

Typically, a time that is sufficient to carry out the morphinone-forming method ranges from about 0.25 hours to about 50 hours; in another embodiment, a time that is sufficient to carry out the carbonyl-forming method ranges from about 0.5 hours to about 25 hours; and in another embodiment, a time that is sufficient to carry out the morphinone-forming method ranges from about 1 hours to about 10 hours.

Typically, a temperature that is sufficient to carry out the morphinone-forming method ranges from about −78° C. to about 130° C.; in another embodiment, a temperature that is sufficient to carry out the morphinone-forming method ranges from about −50° C. to about 50° C.; and in another embodiment, a temperature that is sufficient to carry out the morphinone-forming method ranges from about −40° C. to about 50° C.

The morphinone-forming method can be carried out at reduced pressure, atmospheric pressure or elevated pressure. In one embodiment, the morphinone-forming method is carried out at atmospheric pressure.

In another embodiment, the morphinone-forming method is carried out under an inert atmosphere such as, e.g., $N_2$, He, Ne, Ar, Kr, Xe, or any combination thereof. In one embodiment, the morphinone-forming method is carried out under a $N_2$ atmosphere.

The present invention further relates to compositions comprising a compound of formula (I), a compound of formula $RiSR_2$ and a chlorine-containing compound; wherein $R_1$ and $R_2$ are each independently —$(C_1-C_{20})$alkyl, —$(C_3-C_8)$cycloalkyl or -phenyl; and $R_3$ is a protecting group. These compositions are useful for making a compound of formula (II).

In another embodiment, the invention relates to compositions comprising a compound of formula (I), a compound of formula $R_1SR_2$ and a chlorine-containing compound; wherein $R_1$ and $R_2$ are each independently —$(C_1-C_{20})$alkyl, —$(C_3-C_8)$cycloalkyl or -phenyl; $R_3$ is a protecting group; and the chlorine-containing reagent is trichloroisocyanuric acid, N-chlorosuccinimide, sodium dichloroisocyanurate, 1,3-dichloro-5,5-dimethylhydantoin, $Cl_2$, calcium hypochlorite, or any mixture thereof.

In another embodiment, the invention relates to compositions comprising a compound of formula (I), a compound of formula $R_1SR_2$ and a chlorine-containing compound; wherein $R_1$ and $R_2$ are each independently —$(C_1-C_{20})$alkyl, —$(C_3-C_8)$cycloalkyl or -phenyl; $R_3$ is a protecting group; and the chlorine-containing reagent is trichloroisocyanuric acid, N-chlorosuccinimide, $Cl_2$, or any mixture thereof.

In another embodiment, the invention relates to compositions comprising a compound of formula (I), a compound of formula $R_1SR_2$ and trichloroisocyanuric acid; wherein $R_1$ and $R_2$ are each independently —$(C_1-C_{20})$alkyl, —$(C_3-C_8)$cycloalkyl or -phenyl; and $R_3$ is a protecting group.

In one embodiment, the invention relates to a composition comprising a compound of formula $R_1SR_2$ as defined herein, a chlorine-containing compound and a compound of formula (I), wherein is $R_3$ is -benzyl, —$C(O)(C_1-C_{10})$alkyl, —$C(O)O(C_1-C_{10})$alkyl, —$Si((C_1-C_{10})$alkyl$)_3$, —$Si(aryl)((C_1-C_{10})$ alkyl)$_2$, —Si(aryl)$_2$((C$_1$-C$_{10}$)alkyl), —P(O)((C$_1$-C$_{10}$)alkyl)$_2$, —P(S)((C$_1$-C$_{10}$)alkyl)$_2$, or —S(O)OC$_6$H$_4$-p-CH$_3$.

In another embodiment, the invention relates to a composition comprising a compound of formula R$_1$SR$_2$, a chlorine-containing reagent and a compound of formula (I), wherein R$_3$ is —Si((C$_1$-C$_{10}$)alkyl)$_3$, —Si(aryl)(C$_1$-C$_{10}$)alkyl)$_2$, or —Si(aryl)$_2$(C$_1$-C$_{10}$)alkyl.

In another embodiment, the invention relates to a composition comprising a compound of formula R$_1$SR$_2$, a chlorine-containing reagent and a compound of formula (I), wherein R$_3$ is —Si(C$_1$-C$_{10}$)alkyl)$_3$.

In another embodiment, the invention relates to a composition comprising a compound of formula R$_1$SR$_2$, a chlorine-containing reagent and a compound of formula (I), wherein R$_3$ is —Si(CH$_3$)$_2$(C(CH$_3$)$_3$).

In another embodiment, the invention relates to a composition comprising a compound of formula R$_1$SR$_2$, a chlorine-containing reagent and a compound of formula (I), wherein R$_3$ is —CH$_3$.

In another embodiment, the invention relates to a composition comprising a compound of formula R$_1$SR$_2$, a chlorine-containing reagent and a compound of formula (Ia).

In another embodiment, the compositions comprising a compound of formula (I) or (Ia), a compound of formula R$_1$SR$_2$ and a chlorine-containing reagent further comprise a base. Non-limiting examples of bases include those described in Section 4.2 for the carbonyl-forming method.

In another embodiment, the compositions comprising a compound of formula (I) or (Ia), a compound of formula R$_1$SR$_2$ and a chlorine-containing reagent further comprise an organic solvent. Non-limiting examples of organic solvents include those described in Section 4.2 for the carbonyl-forming method.

The relative molar amounts of the compound of formula (I) or (Ia), the compound of formula R$_1$SR$_2$, the chlorine-containing reagent, the base, if any, and the organic solvent, if any, are those described above for the morphinone-forming method.

4.4. Methods for Making 3-O-Protected Morohinone Dienol Carboxylates

As noted above, the present invention also relates to methods for making a compound of formula (III).

In one embodiment, the present invention relates to a method for making a compound of formula (III), comprising:

(a) allowing a compound of formula (I) to react in the presence of a compound of formula R$_1$SR$_2$ and a chlorine-containing reagent under conditions sufficient to make a compound of formula (II); and (b) allowing the compound of formula (II) to react with a first base and an acylating agent of formula R$_4$C(O)OC(O)R$_4$ or R$_4$C(O)X under conditions sufficient to make the compound of formula (III), wherein R$_1$ and R$_2$ are each independently —(C$_1$-C$_{20}$)alkyl, —(C$_3$-C$_8$)cycloalkyl or -phenyl;

R$_3$ is a protecting group;

R$_4$ is —(C$_1$-C$_{10}$)alkyl; and

X is —Cl, —Br or —I.

The step of allowing a compound of formula (I) to react in the presence of a compound of formula R$_1$SR$_2$ and a chlorine-containing reagent under conditions sufficient to make a compound of formula (II) (the "morphinone-forming step") can be carried out by the methods described in Section 4.3 for the morphinone-forming method.

In one embodiment, the morphinone-forming step is carried out in the presence of a base (the "second base") as described in Section 4.3 when the morphinone-forming method is carried out in the presence of a base. Non-limiting examples of useful second bases include those bases described in Section 4.2 for the carbonyl-forming method. The second base, when used in the morphinone-forming step, can be the same as or different from the first base. In one embodiment, the first base and the second base, when used, are the same.

In one embodiment, the second base when used in the morphinone-forming step is triethylamine or para-N,N-dimethylaminopyridine.

In another embodiment, the second base when used in the morphinone-forming step is triethylamine.

In one embodiment, the amount of second base when used in the morphinone-forming step ranges from about 1.0 to about 15.0 molar equivalents per molar equivalent of the chlorine-containing reagent; in another embodiment, the amount of second base when used in the morphinone-forming step ranges from about 2.0 to about 10.0 molar equivalents per molar equivalent of the chlorine-containing reagent; and in another embodiment, the amount of second base when used in the morphinone-forming step ranges from about 2.5 to about 7.0 molar equivalents per molar equivalent of the chlorine-containing reagent.

The step of allowing the compound of formula (II) to react with a rust base and an acylating agent of formula R$_4$C(O)OC(O)R$_4$ or R$_4$C(O)X under conditions sufficient to make the compound of formula (III) (the "morphinone dienol carboxylate-forming step") can be carried out by methods described below.

In one embodiment, the morphinone dienol carboxylate-forming step comprises the use of a compound of formula (II), wherein R$_3$ is —(C$_1$-C$_{10}$)alkyl, -benzyl, —C(O)(C$_1$-C$_{10}$)alkyl, —C(O)O(C$_1$-C$_{10}$)alkyl), —Si((C$_1$-C$_{10}$)alkyl)$_3$, —Si(aryl)((C$_1$-C$_{10}$)alkyl)$_2$, —Si(aryl)$_2$((C$_1$-C$_{10}$)alkyl), —P(O)((C$_1$-C$_{10}$)alkyl)$_2$, —P(S)((C$_1$-C$_{10}$)alkyl)$_2$, or —S(O)OC$_6$H$_4$-p-CH$_3$.

In one embodiment, the morphinone dienol carboxylate-forming step comprises the use of a compound of formula (II), wherein R$_3$ is —CH$_3$.

In another embodiment, the morphinone dienol carboxylate-forming step comprises the use of a compound of formula (II), wherein R$_3$ is —Si((C$_1$-C$_{10}$)alkyl)$_3$, —Si(aryl)(C$_1$-C$_{10}$)alkyl)$_2$, or —Si(aryl)$_2$(C$_1$-C$_{10}$)alkyl).

In another embodiment, the morphinone dienol carboxylate-forming step comprises the use of a compound of formula (II), wherein R$_3$ is —Si((C$_1$-C$_{10}$)alkyl)$_3$.

In another embodiment, the morphinone dienol carboxylate-forming step comprises the use of a compound of formula (II), wherein R$_3$ is —Si(CH$_3$)$_2$(C(CH$_3$)$_3$).

In one embodiment, the morphinone dienol carboxylate-forming step comprises the use of an acylating agent of formula R$_4$C(O)OC(O)R$_4$.

In another embodiment the morphinone dienol carboxylate-forming step comprises the use of an acylating agent of formula CH$_3$C(O)OC(O)CH$_3$.

In another embodiment, the morphinone dienol carboxylate-forming method comprises an acylating agent of formula R$_4$C(O)X.

In another embodiment, the morphinone dienol carboxylate-forming step comprises the use of an acylating agent of formula R$_4$C(O)X, wherein X is —F, —Cl, —Br or —I.

In another embodiment, the morphinone dienol carboxylate-forming step comprises the use of an acylating agent of formula CH$_3$C(O)Cl.

Non-limiting examples of first bases useful for the morphinone dienol carboxylate-forming step include those discussed in Section 4.2 for the carbonyl-forming method.

In one embodiment, the first base is a trialkylamine, para-N,N-dimethylpyridine or an alkali metal carboxylate.

In another embodiment, the first base is triethylamine.

In another embodiment, the first base is para-N,N-dimethylpyridine.

Acylating agents of formula $R_4C(O)OC(O)R_4$ or $R_4C(O)X$ are commercially available or can be prepared by known methods.

In one embodiment, the amount of acylating agent used in the morphinone dienol carboxylate-forming step ranges from about 1 to about 15 molar equivalent per molar equivalent of the compound of formula (II); in another embodiment, the amount of acylating agent used in the morphinone dienol carboxylate-forming step ranges from about 1 to about 10 molar equivalent per molar equivalent of the compound of formula (II); and in another embodiment, the amount of acylating agent used in the morphinone dienol carboxylate-forming step ranges from about 2 to about 7 molar equivalent per molar equivalent of the compound of formula (M).

In one embodiment, the amount of first base used in the morphinone dienol carboxylate-forming step ranges from about 1 to about 15 molar equivalents per molar equivalent of the acylating agent; in another embodiment, the amount of first base used in the morphinone dienol carboxylate-forming step ranges from about 2 to about 7 molar equivalents per molar equivalent of the acylating agent; and in another embodiment, the amount of first base used in the morphinone dienol carboxylate-forming step ranges from about 3 to about 6 molar equivalents per molar equivalent of the acylating agent.

In one embodiment, the morphinone dienol carboxylate-farming step is carried out in the presence of an organic solvent. Non-limiting examples of useful organic solvents for the morphinone dienol carboxylate-forming step include those discussed in Section 4.2 for the carbonyl-forming method.

In one embodiment, the organic solvent when used in the morphinone dienol carboxylate-forming step is dichloromethane, tetrahydrofuran, methyltetrahydrofuran, toluene, or any mixture thereof.

In one embodiment, the amount of organic solvent when used in the morphinone dienol carboxylate-forming step ranges from about 1 part by weight up to about 100 parts by weight based on the weight of the compound of formula (II); in another embodiment, the amount of organic solvent when used in the morphinone dienol carboxylate-forming step ranges from about 5 parts by weight up to about 50 parts by weight based on the weight of the compound of formula (II); and in another embodiment, the amount of organic solvent when used in the morphinone dienol carboxylate-forming step ranges from about 10 parts by weight up to about 25 parts by weight based on the weight of the compound of formula (II).

In one embodiment, the organic solvent when used in the morphinone dienol carboxylate-forming step is anhydrous. Methods for preparing anhydrous organic solvents are described in Section 4.2 for the carbonyl-forming method.

The morphinone dienol carboxylate-forming step is carried out under conditions that are sufficient to make the morphinone dienol carboxylate. In one non-limiting embodiment, the morphinone dienol carboxylate-forming step is carried out until at least about 80 mole percent of the compound of formula (II) has been converted to the compound of formula (III); in another non-limiting embodiment, the morphinone dienol carboxylate-forming step is carried out until at least about 95 mole percent of the compound of formula (II) has been converted to a compound of formula (III); and in another non-limiting embodiment, the morphinone dienol carboxylate-forming step is carried out until at least about 99 mole percent of the compound of formula (II) has been converted to a compound of formula (III).

The progress of the morphinone dienol carboxylate-forming step can be monitored using conventional analytical techniques comparable to those described in Section 4.2

The morphinone dienol carboxylate-forming step is carried out for a time and at a temperature sufficient to make a compound of formula (III). In one embodiment, a time sufficient to make a compound of formula (III) ranges from about 1 h up to about 50 h; in another embodiment, a time sufficient to make a compound of formula (III) ranges from about 5 h up to about 30 h; and in another embodiment, a time sufficient to make a compound of formula (III) ranges from about 5 h up to about 25 h.

In one embodiment, a temperature sufficient to make a compound of formula (III) ranges from about −78° C. up to about the boiling point of the organic solvent, if used; in another embodiment, a temperature sufficient to make a compound of formula (III) ranges from about −78° C. up to about the 130° C.; in another embodiment, a temperature sufficient to make a compound of formula (III) ranges from about 0° C. up to about 100° C.; and in another embodiment, a temperature sufficient to make a compound of formula (III) ranges from about 20° C. up to about 75° C.

The morphinone dienol carboxylate-forming step can be carried out at reduced pressure, atmospheric pressure or elevated pressure. In one embodiment, the morphinone dienol carboxylate-forming step is carried out at atmospheric pressure.

In one embodiment, the morphinone dienol carboxylate-forming step is carried out under an inert atmosphere such as, e.g., $N_2$, He, Ne, Ar, Kr, Xe, or any combination thereof. In another embodiment, the morphinone dienol carboxylate-forming step is carried out under $N_2$ atmosphere.

In the morphinone dienol carboxylate-forming step, the order of addition of the compound of formula (II), acylating agent, first base and organic solvent, when present, can vary.

In one non-limiting embodiment, the morphinone dienol carboxylate-forming step is carried out by adding the compound of formula (II), optionally in the presence of an organic solvent, to an admixture comprising an acylating agent and a first base, optionally in the presence of an organic solvent.

In another non-limiting embodiment, the morphinone dienol carboxylate-forming step is carried out by adding an admixture comprising an acylating agent and a first base, optionally in the presence of an organic solvent, to a compound of formula (II), optionally in the presence of an organic solvent.

In another non-limiting embodiment, the morphinone dienol carboxylate-forming step is carried out by adding a first base, optionally in the presence of an organic solvent, to an admixture comprising a compound of formula (II), optionally in the presence of an organic solvent, followed by addition of an acylating agent, optionally in the presence of an organic solvent.

In another non-limiting embodiment, the morphinone dienol carboxylate-forming step is carried out by adding an acylating agent, optionally in the presence of an organic solvent, to an admixture comprising a compound of formula (II), optionally in the presence of an organic solvent, followed by addition of a first base, optionally in the presence of an organic solvent.

In one embodiment, the compound of formula (II) is prepared using the morphinone-forming step, and is not isolated before being used in the morphinone dienol carboxylate-forming step.

In another embodiment, the compound of formula (II) is not isolated after the morphinone dienol carboxylate-forming step, and the acylating agent and first base are added to the compound of formula (II), i.e. a "one pot" method.

In another embodiment, the compound of formula (II) is not isolated after the morphinone-forming step, and the acylating agent and first base are added simultaneously to the compound of formula (II).

In another embodiment, the compound of formula (II) is not isolated after the morphinone-forming step, and the acylating agent is added first to the compound of formula (II) followed by addition of the first base.

In another embodiment, the compound of formula (II) is not isolated after the morphinone-forming step, and the first base is added first to the compound of formula (II) followed by addition of the acylating agent.

In another embodiment, the morphinone-forming step further comprises a second base; the compound of formula (II) is not isolated after the morphinone-forming step; and the acylating agent is added to the compound of formula (II) followed by addition of the first base.

In another embodiment, the morphinone-forming step further comprises a second base; the compound of formula (II) is not isolated after the morphinone-forming step; and the acylating agent and first base are added simultaneously to the compound of formula (II); wherein the second base and first base are the same.

In one embodiment, the compound of formula (II) is not isolated after the morphinone-forming step, and the morphinone-forming step comprises the use of a first base and a second base. When the morphinone-forming step comprises the use of a first base and a second base, the first base and second base can be the same or different. In one embodiment, the first base and second base are the same. In another embodiment, the first base and second base are both triethylamine.

In another embodiment, the compound of formula (II) is isolated prior to its use in the morphinone dienol carboxylate-forming step. Methods for isolating the compound of formula (II) include those discussed in Section 4.2 for the ketones or aldehydes formed in the carbonyl-forming method.

If desired, compounds of formula (III) can be isolated and purified by methods comparable to those discussed in Section 4.2 for isolating and purifying the ketones or aldehydes formed in the carbonyl-forming method and/or by methods described below.

In one embodiment, a method for isolating a compound of formula (III) comprises contacting the compound of formula (III) with an organic solvent and water.

For example, the compound of formula (III) can be isolated by contacting an admixture (the "contacting step") comprising the compound of formula (III) and an organic solvent with water that is optionally acidified. When the water used in the contacting step is not acidified, the organic phase is collected, the aqueous phase can be further contacted with organic solvent, and the resultant biphasic admixture can optionally be further treated with a base such as 25% aqueous NaOH to increase the pH of the aqueous phase to within the range of about 7.0 to about 9.0.

When the water used in the contacting step is acidified, the aqueous phase is collected; the aqueous phase is contacted with an organic phase; the resultant biphasic admixture is further treated with a base such as 25% aqueous NaOH to increase the pH of the aqueous phase to within the range of about 7.0 to about 9.0; and the organic phase is collected.

The combined organic phases are concentrated to a residue under reduced pressure, and the resultant residue can be further isolated and purified by methods comparable to those described above in Section 4.2 such as, e.g., distillation, crystallization and/or chromatography.

Non-limiting examples of useful organic solvents for contacting a compound of formula (III) in the presence of water include water-immiscible organic solvents such as straight-chain and branch-chain aliphatic ($C_4$-$C_{10}$)hydrocarbons such as butanes, pentanes, hexanes, heptanes, octanes, nonanes, decanes; cyclic aliphatic ($C_4$-$C_7$)hydrocarbons such as cyclobutane, cyclopentane, cyclohexane and cycloheptane; aromatic hydrocarbons such as benzene, toluene and xylene, each of which can be substituted with one or more -halo or -hydroxy groups; ($C_1$-$C_3$)hydrocarbons substituted with two or more -halo groups such as dichloromethane, chloroform and carbon tetrachloride; dialkyl ethers such as diethyl ether, diisopropyl ether, dibutyl ethers and methyl butyl ethers; ethyl acetate; and any mixture thereof. In one embodiment, the organic solvent is dichloromethane.

Compounds of formula (III) are useful for making morphine alkaloids such as naloxone, naltrexone and oxycodone by methods known in the art (see, e.g., U.S. Pat. No. 6,013,796 to Huang et al.).

If desired, the $R_3$ protecting group of the compound of formula (III) can be removed and replaced with a group such as —H (the "deprotection step"). Typically, the deprotection step is not carried out until completing other chemical processes that might be adversely affected by the presence of a hydroxyl group on the benzylic ring of the morphine alkaloid. Methods for removing specific protecting groups from morphine alkaloids are described, e.g., in U.S. Pat. No. 4,472,253 to Schwartz (where $R_3$ is -alkyl); U.S. Pat. No. 5,112,975 to Wallace (where $R_3$ is -carbonate); and U.S. Pat. No. 6,008,355 to Huang et al. (where $R_3$ is -acyl); or by methods known in the art for deprotecting phenols (see, e.g., Greene et al., *Protective Groups in Organic Synthesis* 143-170 (1991), each reference being incorporated herein by reference).

As noted above, the present invention also relates to novel compounds of formula (III), wherein $R_3$ is —Si(($C_1$-$C_{10}$)alkyl)$_3$, —Si(aryl)($C_1$-$C_{10}$)alkyl)$_2$, or —Si(aryl)$_2$($C_1$-$C_{10}$)alkyl; and $R_4$ is —($C_1$-$C_{10}$)alkyl.

In one embodiment, the present invention relates to novel compounds of formula (III), where $R_3$ is —Si(($C_1$-$C_{10}$)alkyl)$_3$.

In another embodiment, the present invention also relates to novel compounds of formula (III), where $R_3$ is —Si($CH_3$)$_2$(C($CH_3$)$_3$).

In another embodiment, the present invention also relates to novel compounds of formula (III), where $R_4$ is —$CH_3$.

The novel compounds of formula (III) can be prepared by allowing a compound of formula (II), where $R_3$ is —Si(($C_1$-$C_{10}$)alkyl)$_3$, —Si(aryl)($C_1$-$C_{10}$)alkyl)$_2$, or —Si(aryl)$_2$($C_1$-$C_{10}$)alkyl) to react with a first base and an acylating agent under conditions sufficient to make the compound of formula (III) as described above.

The following examples are set forth to assist in understanding the invention and do not limit the invention described and claimed herein. Such variations of the invention, including the substitution of all equivalents now known or later developed, which would be within the purview of those skilled in the art, and changes in formulations or minor changes in experimental design, fall within the scope of the present invention.

5. EXAMPLES

5.1. Example 1

Synthesis of 3-O-Bis(dimethyl-t-butyl)silylmorphine

A solution of dimethyl-t-butylsilylchloride (0.115 g, 0.76 mmol) in tetrahydrofuran (76 mL) (Aldrich) was added over about 5 min to a solution of morphine base (20.38 g, 71 mmol), imidazole (14.59 g; 214 mmol) and dimethylformamide ("DMF") (100 ml) at 25° C. under $N_2$ atmosphere. The resultant green solution was stirred at 25° C. for 24 h and concentrated under reduced pressure and at 40° C. The resultant viscous mixture was added to deionized water (500 g) at 25° C., and the resultant white precipitate was collected via filtration. The solids were dissolved in dichloromethane (100 ml), and the resultant organic phase was collected. The organic phase was dried over sodium sulfate, filtered, and the filtrate concentrated under reduced pressure at 40° C. The resultant residue was recrystallized from boiling heptane (75 ml) to afford 3-O-bis(dimethyl-t-butyl)silylmorphine as white crystals. Yield: 13.60 g (34 mmol, 48%).

5.2. Example 2

One-pot Synthesis of Codeinone Dienol Acetate

Preparation of Codeinone:

Trichloroisocyanuric acid (2.30 g, 3.8 mmol) was charged to a 100 ml round-bottom flask equipped with a distillation head, and the contents of the flask were cooled to −30° C. under an $N_2$ atmosphere. Anhydrous dichloromethane (15 ml) was charged to the flask, and the resultant suspension was stirred for 30 min at −30° C. A solution of codeine (2.97 g, 9.9 mmol) in anhydrous dichloromethane (15 ml) was added drop-wise over about 5 min to the suspension, and the contents of the flask were mixed for about 30 min at −30° C. The resultant milky suspension was maintained at −30° C., and neat triethylamine (6.91 ml, 50 mmol) was added drop-wise over about 10 min. The resultant light brown suspension was warmed to 10° C. over 2 h at which time the conversion of codeine to codeinone was complete.

Preparation of Codeinone Dienol Acetate:

The brown suspension from above was allowed to warm to room temperature, and neat acetic anhydride (4.68 ml, 50 mmol) was added. The contents of the flask were warmed to about 50° C., and about 90% of the dichloromethane was removed by distillation. The resultant slurry was allowed to cool to about 25° C. and mixed for 17 h at 25° C. at which time the conversion of codeinone to codeinone dienol acetate was complete.

Dichloromethane (20 ml) was added to the reaction mixture and the mixture cooled to 0° C. A solution of 3 ml of 88% (w/w) formic acid in 20 ml of water at about 0° C. was added to the cooled mixture, and the biphasic mixture was agitated for 5 min at 0° C. The resultant organic phase was collected and washed with a solution 1 ml of 88% (w/w) formic acid in 20 ml of water. The aqueous layers were combined and cooled to about 0° C. Dichloromethane (20 ml) was added, then 25% (w/w) aqueous sodium hydroxide was added until the pH of the aqueous phase was 8.75. The aqueous layer was collected, and extracted with dichloromethane (20 ml). The combined organic layers were dried over sodium sulfate, filtered, and concentrated under reduced pressure at 30° C. The resultant oily residue was further dried at 40 Torr at 30° C. to provide codeinone dienol acetate as a light brown solid. Yield: 2.82 g (83 mmol; 84%).

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed is:

1. A composition comprising trichloroisocyanuric acid, a base, a compound of formula $R_1SR_2$, wherein $R_1$ and $R_2$ are each independently —$(C_1$-$C_{20})$alkyl, —$(C_3$-$C_8)$cycloalkyl, or -phenyl, and a compound of formula (I):

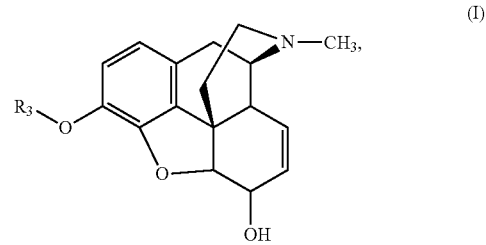

wherein $R_3$ is a protecting group selected from —$(C_1$-$C_{10})$alkyl, -benzyl, —C(O)$(C_1$-$C_{10})$alkyl, —C(O)O$(C_1$-$C_{10})$allyl, —Si$((C_1$-$C_{10})$alkyl$)_3$, —Si(aryl)$((C_1$-$C_{10})$alkyl$)_2$, —Si(aryl)$_2((C_1$-$C_{10})$alkyl), —P(O)$((C_1$-$C_{10})$alkyl$)_2$, —P(S)$((C_1$-$C_{10})$alkyl$)_2$, and —S(O)O$C_6H_4$-p-$CH_3$.

2. The composition of claim 1, wherein $R_1$ is —$CH_3$ and $R_2$ is —$(C_{1-2})$alkyl.

3. The composition of claim 1, wherein the base is selected from triethylamine, diisopropylethylamine, pyridine, dimethylpyridine, dimethylaminopyridine, and any mixture thereof.

4. The composition of claim 1, wherein $R_3$ is —$CH_3$ or —Si$(CH_3)_2(C(CH_3)_3)$.

5. The composition of claim 1, wherein the amount of the compound of formula (I) ranges from about 1.0 to about 9.0, from about 2.0 to about 5.0, or from about 2.0 to about 4.0 molar equivalents per molar equivalent of trichloroisocyanuric acid.

6. The composition of claim 1, wherein the amount of the compound of formula $R_1SR_2$ ranges from about 1.0 to about 9.0, from about 2.0 to about 5.0, or from about 2.5 to about 3.5 molar equivalents per molar equivalent of trichloroisocyanuric acid.

7. The composition of claim 1, wherein the compound of formula (I) is a compound of formula (Ia):

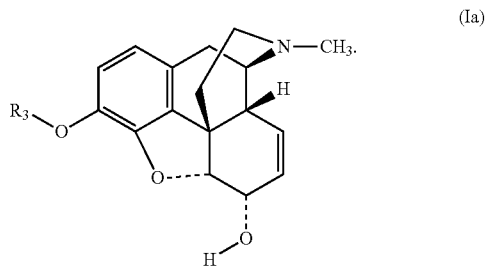

8. A composition comprising a compound of formula (I):

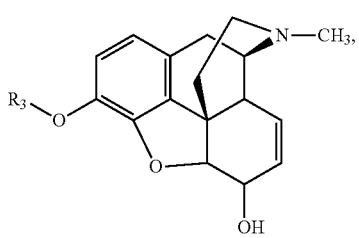

(I)

a compound of formula $R_1SR_2$, and a chlorine-containing compound selected from trichloroisocyanuric acid, sodium dichloroisocyanurate, 1,3-dichloro-5,5-dimethylhydantoin, $Cl_2$, calcium hypochlorite, and any mixture thereof; wherein
- $R_1$ and $R_2$ are each independently —$(C_1-C_{20})$alkyl, —$(C_3-C_8)$cycloalkyl, or -phenyl; and
- $R_3$ is a protecting group selected from —$(C_1-C_{10})$alkyl, -benzyl, —$C(O)(C_1-C_{10})$alkyl, —$C(O)O(C_1-C_{10})$alkyl, —$Si((C_1-C_{10})$alkyl$)_3$, -Si(aryl)$((C_1-C_{10})$alkyl$)_2$, —Si(aryl)$_2((C_1-C_{10})$alkyl), —$P(O)((C_1-C_{10})$alkyl$)_2$, —$P(S)((C_1-C_{10})$alkyl$)_2$, and —$S(O)OC_6H_4$-p-$CH_3$.

9. The composition of claim 8, wherein $R_1$ is —$CH_3$ and $R_2$ is —$(C_{12})$alkyl.

10. The composition of claim 8, wherein the chlorine-containing compound is selected from trichloroisocyanuric acid, sodium dichloroisocyanurate, 1,3-dichloro-5,5-dimethylhydantoin, calcium hypochlorite, and any mixture thereof.

11. The composition of claim 8, wherein $R_3$ is —$CH_3$ or —$Si(CH_3)_2(C(CH_3)_3)$.

12. The composition of claim 8, further comprising a base.

13. The composition of claim 12, wherein the base selected from triethylamine, diisopropylethylamine, pyridine, dimethylpyridine, dimethylaminopyridine, and any mixture thereof.

14. The composition of claim 8, wherein the amount of the compound of formula (I) ranges from about 1.0 to about 9.0, from about 2.0 to about 5.0, or from about 2.0 to about 4.0 molar equivalents per molar equivalent of the chlorine-containing compound.

15. The composition of claim 8, wherein the amount of the compound of formula $R_1SR_2$ ranges from about 1.0 to about 9.0, from about 2.0 to about 5.0, or from about 2.5 to about 3.5 molar equivalents per molar equivalent of the chlorine-containing compound.

16. The composition of claim 8, wherein the compound of formula (I) is a compound of formula (Ia):

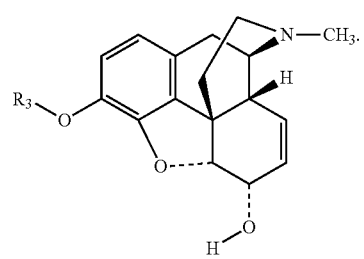

(Ia)

17. The composition of claim 16, wherein $R_1$ is —$CH_3$ and $R_2$ is —$(C_{12})$alkyl.

18. The composition of claim 16, wherein the chlorine-containing compound is selected from trichloroisocyanuric acid, sodium dichloroisocyanurate, 1,3-dichloro-5,5-dimethylhydantoin, calcium hypochlorite, and any mixture thereof.

19. The composition of claim 16, wherein $R_3$ is —$CH_3$ or —$Si(CH_3)_2(C(CH_3)_3)$.

20. The composition of claim 16, further comprising a base.

21. The composition of claim 20, wherein the base selected from triethylamine, diisopropylethylamine, pyridine, dimethylpyridine, dimethylaminopyridine, and any mixture thereof.

22. The composition of claim 16, wherein the amount of the compound of formula (Ia) ranges from about 1.0 to about 9.0, from about 2.0 to about 5.0, or from about 2.0 to about 4.0 molar equivalents per molar equivalent of the chlorine-containing compound.

23. The composition of claim 16, wherein the amount of the compound of formula $R_1SR_2$ ranges from about 1.0 to about 9.0, from about 2.0 to about 5.0, or from about 2.5 to about 3.5 molar equivalents per molar equivalent of the chlorine-containing compound.

* * * * *